United States Patent
Nerot et al.

(10) Patent No.: US 9,622,869 B2
(45) Date of Patent: Apr. 18, 2017

(54) MODULAR HUMERAL PROSTHESIS FOR AN INVERTED SHOULDER PROSTHESIS

(75) Inventors: Cecile Nerot, Reims (FR); Didier Capon, Sautron (FR); Ludwig Seebauer, Forstinning (DE); Anders Ekelund, Bromma (SE); Lieven De Wilde, Gent (BE); Michael Wirth, San Antonio, TX (US); David Collins, Little Rock, AR (US); Laurent Lafosse, Annecy le Vieux (FR); Didier Poncet, Bron (FR)

(73) Assignees: Cecile Nerot, Raynham, MA (US); Didier Capon, Raynham, MA (US); Ludwig Seebauer, Raynham, MA (US); Anders Ekelund, Raynham, MA (US); Lieven De Wilde, Raynham, MA (US); Laurent Lafosse, Raynham, MA (US); DePuy Synthes Products, Inc., Raynham, MA (US)

( * ) Notice: Subject to any disclaimer, the term of this patent is extended or adjusted under 35 U.S.C. 154(b) by 1841 days.

(21) Appl. No.: 11/577,966

(22) PCT Filed: Oct. 25, 2005

(86) PCT No.: PCT/FR2005/002663
§ 371 (c)(1),
(2), (4) Date: Apr. 28, 2009

(87) PCT Pub. No.: WO2006/045949
PCT Pub. Date: May 4, 2006

(65) Prior Publication Data
US 2009/0210065 A1  Aug. 20, 2009

(30) Foreign Application Priority Data

Oct. 25, 2004  (FR) ...................................... 04 11366

(51) Int. Cl.
*A61F 2/40* (2006.01)
*A61F 2/30* (2006.01)

(52) U.S. Cl.
CPC .............. *A61F 2/4014* (2013.01); *A61F 2/40* (2013.01); *A61F 2/4059* (2013.01);
(Continued)

(58) Field of Classification Search
CPC ................. A61F 2002/4022; A61F 2002/4074
(Continued)

(56) References Cited

U.S. PATENT DOCUMENTS 5,314,479 A    5/1994  Rockwood, Jr.
5,358,526 A   10/1994  Tornier
(Continued)

FOREIGN PATENT DOCUMENTS

DE    19841612 A1    3/2000
EP     0339530 A2   11/1989
(Continued)

OTHER PUBLICATIONS

Translation of FR2821545.*
(Continued)

*Primary Examiner* — Thomas J Sweet
*Assistant Examiner* — Megan Wolf

(57) ABSTRACT

The invention relates to a modular humeral prosthesis for an inverse shoulder prosthesis, comprising an anatomical shaft (1) and a separable epiphyseal head (2) which may be angularly orientated by rotation about the longitudinal axis (XX) of the anatomical shaft. The anatomical shaft and the epiphyseal head comprise complementary angular indexing means (11, 28) for relative rotational fixation.

13 Claims, 4 Drawing Sheets

Figure 1:
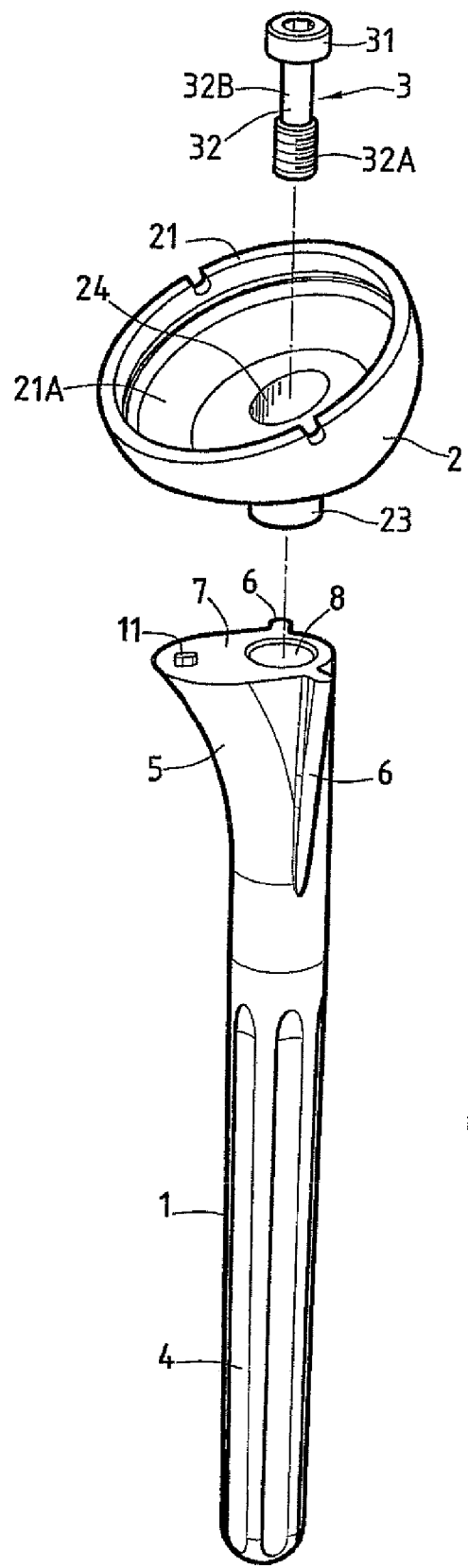

(52) U.S. Cl.
CPC .......... *A61F 2002/3054* (2013.01); *A61F 2002/30617* (2013.01); *A61F 2002/30714* (2013.01); *A61F 2002/4022* (2013.01); *A61F 2002/4074* (2013.01); *A61F 2250/0089* (2013.01); *A61F 2250/0097* (2013.01)

(58) Field of Classification Search
USPC ............................................ 623/19.11–19.14
See application file for complete search history.

(56) References Cited

U.S. PATENT DOCUMENTS

| | | | |
|---|---|---|---|
| 5,910,171 A | 6/1999 | Kummer | |
| 6,790,234 B1 | 9/2004 | Frankle | |
| 6,863,690 B2 * | 3/2005 | Ball et al. | 623/19.11 |
| 7,169,184 B2 | 1/2007 | Dalla Pria | |
| 7,758,650 B2 | 7/2010 | Dews | |
| 2001/0054624 A1 | 12/2001 | Jourdin | |
| 2004/0064187 A1 | 4/2004 | Ball | |
| 2004/0064190 A1 * | 4/2004 | Ball et al. | 623/19.14 |
| 2004/0143335 A1 | 7/2004 | Dews | |
| 2004/0220674 A1 * | 11/2004 | Pria | 623/19.12 |
| 2011/0060417 A1 | 3/2011 | Simmen | |

FOREIGN PATENT DOCUMENTS

| | | |
|---|---|---|
| EP | 0679375 A1 | 11/1995 |
| EP | 0815810 A1 | 1/1998 |
| EP | 1402854 A | 3/2004 |
| EP | 1402854 A2 | 3/2004 |
| EP | 1472999 A1 | 11/2004 |
| FR | 2579454 A1 | 10/1986 |
| FR | 2699400 A1 | 6/1994 |
| FR | 2821545 A | 9/2002 |
| FR | 2821545 A1 | 9/2002 |
| WO | 9725943 A1 | 7/1997 |
| WO | WO 9725943 A1 | 7/1997 |
| WO | WO 03005933 A2 | 1/2003 |
| WO | WO 2006045949 A2 | 5/2006 |
| WO | WO 2006045949 A3 | 8/2006 |

OTHER PUBLICATIONS

Translation of FR 2579454.*
PCT Written Opinion, 6 pages.
Argomedical AG; German Patent No. DE19841612A1; Mar. 16, 2000 English Abstract; Derwent World Patents Index; © 2010 Derwent Information Ltd. Dialog® File No. 351 Accession No. 10388629.
S +G Implants Gmbh, European Patent No. EP0339530A2; Nov. 2, 1989 English Abstract; MicroPatent Report; 2010 MicroPatent LLC.
EUROS Société Anonyme ; European Patent No. EP0679375A1, Nov. 2, 1995; English Abstract; MicroPatent Report; 2010 MicroPatent LLC.
Tornier SA; European Patent No. EP0815810A1, Jan. 7, 1998; English Abstract; Derwent World Patents Index; © 2010 Derwent Information Ltd. Dialog® File No. 351 Accession No. 9059091.
Rambert Andre; French Patent No. FR 2579454A1, Oct. 3, 1986; English Abstract; Derwent World Patents Index; © 2010 Derwent Information Ltd. Dialog® File No. 351 Accession No. 3843947.
Medinov (S.A.); French Patent No. FR2699400A1, Jun. 24, 1994; English Abstract; Derwent World Patents Index; © 2010 Derwent Information Ltd. Dialog® File No. 351 Accession No. 6838357.
Aston Medical Limited, French Patent No. FR2821545A1, Sep. 6, 2002; English Abstract; Derwent World Patents Index; © 2010 Derwent Information Ltd. Dialog® File No. 351 Accession No. 12783035.
U.S. Appl. No. 12/088,907, filed Feb. 9, 2009; Office Action dated Sep. 10, 2009.
U.S. Appl. No. 12/088,907, filed Feb. 9, 2009; Final Office Action dated Mar. 4, 2010.
Duocentric®, Product Information Literature, Aston-Medical—Saint Etienne, France—to the best of our knowledge, 2007.

* cited by examiner

MODULAR HUMERAL PROSTHESIS FOR AN INVERTED SHOULDER PROSTHESIS

The present invention relates to a modular humeral prosthesis for an inverted shoulder prosthesis.

Shoulder prostheses consisting of a humeral prosthesis of which the epiphyseal portion cooperates with a mating deltoid component are known. In particular, anatomical shoulder prostheses in which the humeral prosthesis head is convex are known. These prostheses respect the orientation and the centre of rotation of actual joints. However, and in particular if the cap of the rotators is broken (partially or completely), prostheses of this type prevent elevation of the arm.

In order to re-establish the range of internal rotation of the arm (in particular elevation and abduction), the anatomical prosthesis is replaced by an inverted prosthesis in which the epiphyseal head of the humeral prosthesis is concave. An inverted prosthesis of this type displaces the centre of rotation of the shoulder and this increases the lever arm of the deltoid muscle and thus facilitates elevation of the arm. However, this displacement of the centre of rotation partially limits the internal and external rotations of the arm. In order to promote the internal rotation (which allows the patient to place his hand on his back), the epiphyseal head will be positioned with a retroversion of approximately 0° (frontal plane).

In addition to displacing the centre of rotation of the joint, the inverted shoulder prosthesis changes the angle of retroversion of the prosthesis relative to the shoulders. This modification to the shoulder retroversion angle varies from one patient to another. Therefore, when an inverted shoulder prosthesis is put into position, it has to be suitably orientated relative to the patient's individual anatomy. Similarly, it is desirable that the inverted prosthesis be put into position in such a way that the displacement of the centre of rotation of the shoulder does not cause an excessive distension of the deltoid muscle tendons.

In order to produce inverted shoulder prostheses, it has been proposed to use a single-piece humeral prosthesis of which the rod intended to cooperate with the humerus is generated by revolution and, in particular, is conical. A humeral prosthesis of this type has the advantage of being able to be orientated as desired relative to the humerus, but has the drawback of not being rotationally blocking with respect to the bone, with the result that the prosthesis is able to move and thus become dislodged over a period of time.

To overcome this drawback, it has been proposed to use a humeral prosthesis of which the rod has an anatomical shape, in other words a rod of which the cross-section cooperates with that of the metaphyseal portion of the medullary canal in a well-defined position. With an anatomical humeral rod of this type, however, it is necessary to be able to orientate the epiphyseal head of the prosthesis by rotation around the longitudinal axis of the rod. A modular humeral rod consisting of an anatomical rod and a separable epiphyseal head mounted on the anatomical rod by means of a ball joint, for example, has been proposed for this purpose (EP 1 402 805). This inverted shoulder prosthesis has the drawback of having an epiphyseal head which extends well above the epiphysis of the humerus (outside the humeral bone). This significantly increases the distance between the humerus and the glenoid cavity, over-tensing the deltoid muscle.

To avoid excessive extension of the deltoid muscle ligaments, the patent application US-2004/064187, in particular, has proposed a modular humeral rod for an inverted shoulder prosthesis comprising an anatomical rod on which is mounted a epiphyseal head designed to be integrated inside the epiphysis of the humerus and which can receive either a humeral head for an anatomical joint or a humeral head which mates with a concave joint for an inverted prosthesis. The epiphyseal head of this prosthesis can be orientated by rotation around the longitudinal axis of the humeral rod and can be locked in position relative to the humerus by means of vertical ribs provided in the epiphyseal head and which cooperate with the internal wall of the humeral canal. This prosthesis has the drawback of not having means for easy adjustment of the orientation of the epiphyseal head relative to the anatomical rod. One of the features of inverted shoulder prostheses equipped with an anatomical rod is that the orientation of the epiphyseal head relative to the anatomical rod has to be adapted to each patient. This orientation, which corresponds to the joint retroversion angle, can vary from 10° to 30°, depending on the patient and, in particular, on his age. It is therefore important to be able to adapt and control the orientation of the angle of the epiphyseal head relative to the anatomical rod in each individual case. In addition, when the prosthesis is in position, the angular adjustment of the epiphyseal head relative to the rod has to be locked to prevent it from becoming dislodged over a period of time.

The problem of locking the epiphyseal head in position relative to the rod could be solved by using single-piece anatomical humeral rods. However, the dimensions of the anatomical rod have to be adapted to the patient's size. In addition, the use of single-piece anatomical humeral rods would necessitate the provision of a very large number of rods each corresponding to a size and a retroversion angle. To reduce the number of prostheses required to be able to meet the requirements of all patients, therefore, it is desirable to have modular prostheses in which an epiphyseal head can be combined with an anatomical rod of adapted size, and the epiphyseal head can be orientated precisely relative to the anatomical rod when the prostheses is at rest and this orientation is secured.

In addition to this problem of reducing the number of parts required to meet all the requirements, it is desirable that the prosthesis can be removed in the event of an overhaul. Therefore, the humeral rod (adjusted angularly relative to the epiphysis) must never laterally exceed the epiphysis to allow extraction of the implant.

The object of the present invention is to overcome the drawbacks of known prostheses by proposing a modular humeral rod for an inverted shoulder prosthesis, which allows the epiphyseal head to be orientated precisely and securely relative to the metaphyseal portion of the anatomical rod (to optimize the internal rotation of the humerus), which may be extractable and which, when in position, is completely within the humerus to avoid over-tensing of the deltoid.

The invention accordingly relates to a modular humeral prosthesis for an inverted shoulder prosthesis comprising an anatomical rod which has an anatomical metaphyseal portion and a separable epiphyseal head which can be orientated angularly by rotation around the longitudinal axis of the anatomical rod, the anatomical rod and the epiphyseal head comprising mating means for angular indexing and for the mutual rotational blocking thereof.

The mating means for indexing and rotational blocking are, for example, on the one hand a plurality of notches provided in a contact surface of the epiphyseal head making contact with the numeral rod, disposed in a radial angular distribution around the longitudinal axis of the anatomical rod and, on the other hand, a lug carried by the other contact surface of the anatomical rod making contact with the epiphyseal head and capable of cooperating with said notches.

Preferably, the anatomical rod comprises at least one longitudinal rib for rotational blocking.

Preferably, the anatomical rod and the epiphyseal head comprise mating means for locating and guiding in rotation, and the epiphyseal head and the anatomical rod are joined together by a coaxial screw to the means of guidance in rotation.

Preferably, the joint between the anatomical rod and the epiphyseal head is intended to be located inside the humerus when the prosthesis is in position in order to respect the deltoid tension. It is therefore preferable that the contact surface of the epiphyseal head extends laterally beyond the anatomical rod.

Figure 2:
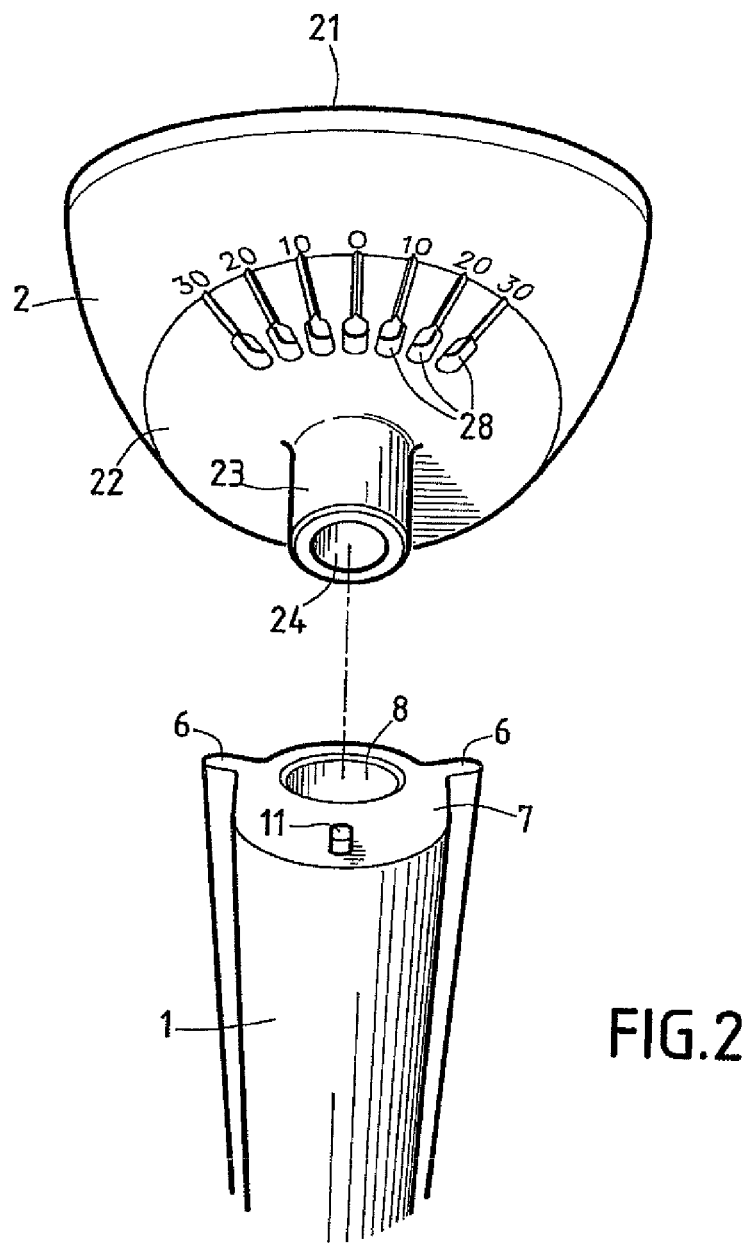
Figure 3:
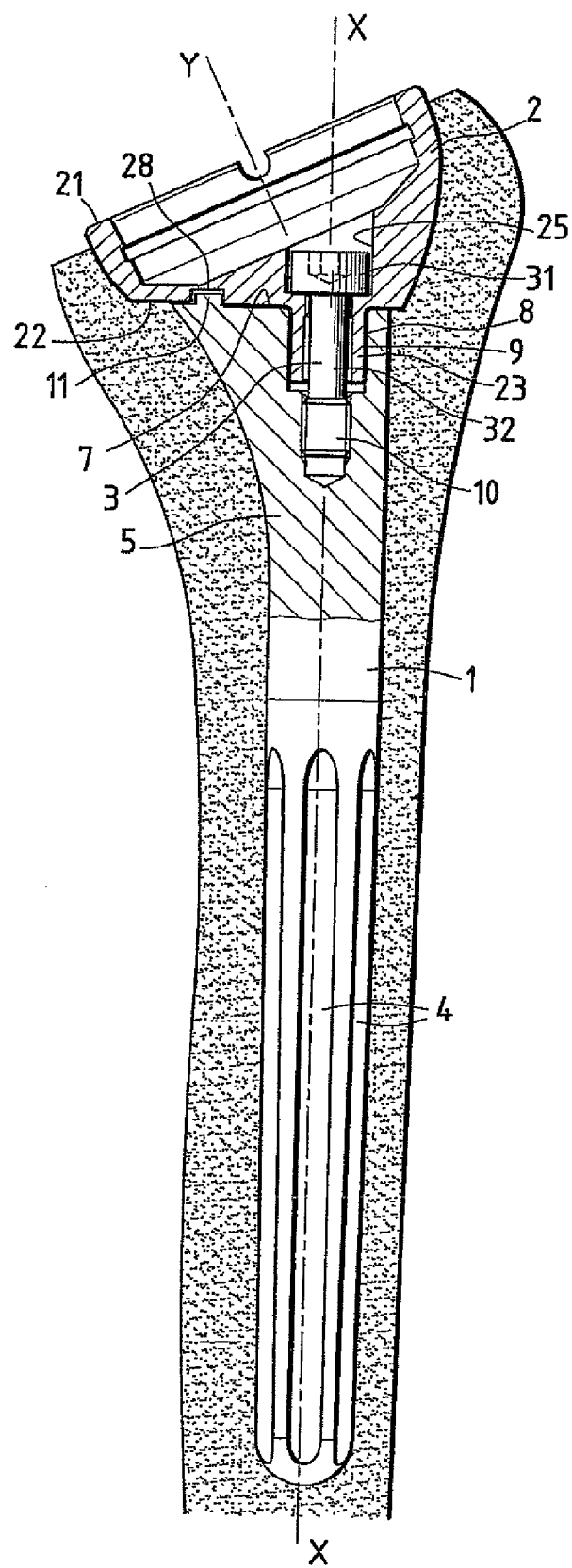

The invention will now be described in greater detail but in a non-limiting manner with reference to the accompanying figures, in which:

FIG. 1 is an exploded view of a modular humeral prosthesis for an inverted shoulder prosthesis, FIG. 2 is an enlarged view from below of the epiphyseal head and the upper portion of the anatomical rod of a modular humeral prosthesis for an inverted shoulder prosthesis, FIG. 3 is an exploded schematic section of a modular humeral prosthesis for an inverted shoulder prosthesis in position within a humerus.

Figure 4:
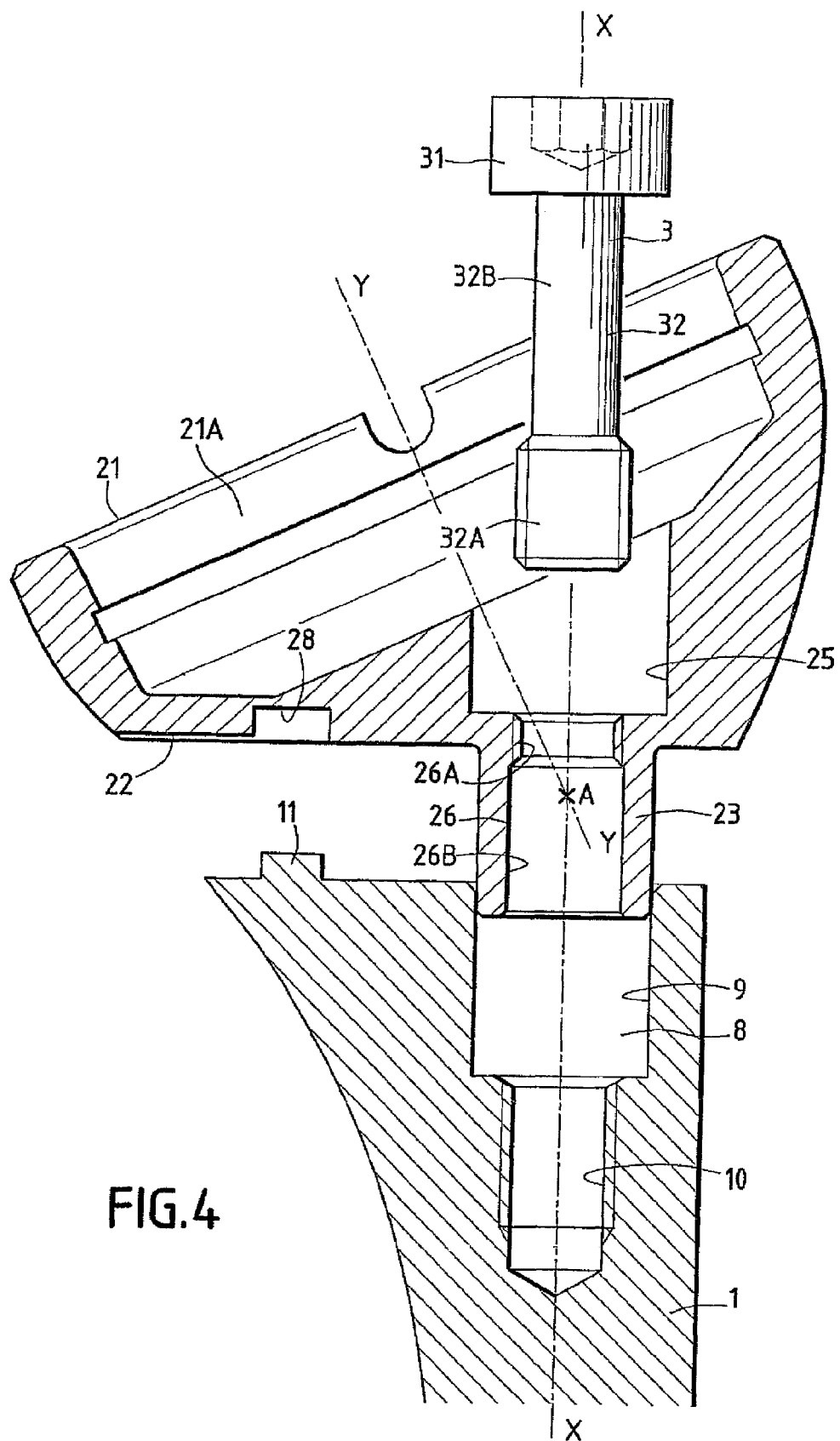

FIG. 4 is an enlarged longitudinal section of the upper portion of the modular humeral prosthesis in FIG. 3.

The modular humeral prosthesis for an inverted shoulder prosthesis shown in FIG. 1 comprises an anatomical rod 1, a separable epiphyseal head 2 which is positioned at the upper end (or proximal extremity) of the anatomical rod 1, and a screw 3 for connecting the epiphyseal head 2 to the rod 1.

The anatomical rod of which the shape is known per se comprises a generally cylindrical stem 4 which is extended in its upper portion by a metaphyseal portion 5 which flares upwardly so as to have a shape which is adapted to the form of the epiphyseal joint of a humerus with the metaphysis of this humerus. This head 5 constitutes the proximal extremity of the anatomical rod, the lateral wall of the head 5 of the anatomical rod comprises ribs 6 for blocking in position relative to a humerus in which the rod is implanted.

The proximal extremity of the anatomical rod 1 is limited by a planar surface 7 which corresponds to a section perpendicular to the longitudinal axis of the anatomical rod. A hole 8 extending within the anatomical rod and parallel to the axis of this rod is drilled perpendicularly to the surface 7 delimiting the proximal extremity. The hole 8 comprises a first bore 9 followed by a screw-threaded hole of smaller diameter 10. Preferably, the hole 8 and the stem 4 of the anatomical rod are coaxial. The surface 7 further comprises a lug 11 which projects longitudinally relative to the metaphyseal rod.

The epiphyseal head 2 is a portion of a sphere delimited by an equatorial plane 21 and a plane forming an acute angle with an equatorial plane. Below the equatorial plane 21, the epiphyseal head 2 comprises a bowl 21A intended to receive a polyethylene or ceramic cup. This cup is the part which is intended to cooperate with the mating portion of the prosthesis which will be fixed to the scapula. The plane forming an acute angle with the equatorial plane defines a polar surface 22 intended to come into contact with the end surface 7 of the anatomical metaphyseal rod 1.

The polar surface 22 comprises a cylindrical lug 23 which projects from the polar surface 22 and is perpendicular thereto. The size of this cylindrical lug 23 is adapted so that it can cooperate with the greater diameter bore 9 of the axial hole 8 in the anatomical rod and thus locate the epiphyseal head relative to the anatomical rod. An axial hole 24 for receiving a screw 3 extends through the cylindrical lug 23, the screw 3 extending both in the hole 24 in the epiphyseal head and in the hole 8 in the anatomical rod so that it will be screwed into the screw-threaded portion 10 of the hole 8. The hole 24 comprises a first portion 25 of greater diameter intended to receive the head 31 of the screw and a portion of smaller diameter 26 intended to receive the body 32 of the screw 3. The cylindrical lug 23 and the hole 8 constitute means for locating and guiding in rotation the epiphyseal head relative to the anatomical rod.

The portion of smaller diameter 26 comprises a first portion 26A of short length having a diameter and a screw thread identical to the diameter and screw thread of the screw-threaded portion 10 of the axial hole 8, the metaphyseal rod and a second portion 26B of greater length extending to the point where the hole emerges at the end of the cylindrical lug 23 and of which the diameter is greater than or equal to the external diameter of the screw-threaded portion of the screw 3. The body 32 of the screw 3 comprises, at its extremity, a screw-threaded end 32A which is capable of cooperating with the screw thread of the screw-threaded portion 10 of the axial hole 8 in the metaphyseal rod, and a stem 32B connecting the head 31 of the screw 3 to the screw-threaded end, and having a diameter smaller than the internal diameter of the first screw-threaded portion 26A of the portion of smaller diameter 26 of the hole 24 in the epiphyseal head.

With this arrangement, the epiphyseal head is completely separated from the anatomical rod by unscrewing the screw. In order to put the screw in position, it first has to be screwed into the screw-threaded portion 26A of the hole in the epiphyseal head. This has the advantage of making the screw integral with this epiphyseal head while leaving it free in rotation and in translation over a specific length and thus facilitates manipulation by the surgeon who is putting the prosthesis in position.

The polar surface 22 comprises a plurality of notches 28 disposed radially relative to the axis of the cylindrical lug 23 and at a distance from this lug such that, when the cylindrical lug 23 is disposed inside the hole 8 of the anatomical rod 1, the lug 11 situated on the surface 7 of the proximal extremity of the anatomical rod 1 can cooperate with a notch 28. These notches are arranged at 10° from one another in a fan and are complemented by markings which allow the position of the epiphyseal head 2 relative to the anatomical rod 1 to be determined when the epiphyseal head is disposed on the anatomical rod and the lug 11 is within a notch 28.

In addition, the plane defining the polar surface 22 is selected so that the diameter of this polar surface is sufficient for the polar surface 22 to extend laterally beyond the surface 7 of the proximal extremity of the anatomical rod, whatever the orientation of the epiphyseal head relative to the anatomical rod. As a result, when the prosthesis is in position in a humerus, the re-growing bone does not form bands which extend beyond the proximal extremity of the anatomical rod and therefore does not prevent extraction of the prosthesis.

Referring to FIG. 4, the epiphyseal head 2 is able to rotate about the longitudinal axis XX of the anatomical rod. The axis YY of the epiphyseal head perpendicular to the equatorial plane 21 intersects the longitudinal axis XX of the anatomical rod 1 at a point A preferably located on a surface defined by the contact between the proximal face 7 of the anatomical rod 1 and the polar face 22 of the epiphyseal head 2.

Finally, FIG. 3 shows that the length of the anatomical rod and the dimensions of the epiphyseal head are selected so that, when the prosthesis is in position, the epiphyseal head is completely included in the epiphysis of the humerus.

In order to put a prosthesis of this type in position, the surgeon begins by preparing the humerus by producing, in a known manner, an axial hole adapted to receive an anatomical humeral rod and an epiphyseal head. Then, using an appropriate gauge, he determines the retroversion which the epiphyseal head will have to perform relative to the anatomical humeral rod.

The surgeon then puts in position the anatomical rod then the epiphyseal head while orientating it at a predetermined angle and immobilises it in rotation by causing the lug 11 of the proximal extremity of the anatomical rod to cooperate with the appropriate groove 28 in the polar surface 22 of the epiphyseal head. He finally tightens the screw 3 to lock the assembly.

The invention claimed is:

1. A modular reverse humeral prosthesis for implantation at least in part within a humerus, comprising:
   an anatomical stem having a longitudinal axis and an axial stem hole parallel to the longitudinal axis, the stem hole having an internally threaded portion; wherein the anatomical stem also has a flared metaphyseal portion;
   a separable epiphyseal head having a socket configured to receive a cup and a head hole that communicates with the socket, the epiphyseal head being rotatable about the longitudinal axis of the stem such that the epiphyseal head and stem can be assembled at a plurality of angular positions, the head hole configured such that the head hole and the stem hole are aligned when the epiphyseal head and the stem are assembled, the head hole having an internally threaded portion; and
   a screw comprising a head, a threaded portion having a screw thread that cooperates with the internally threaded portion of the head hole and the internally threaded portion of the stem hole, and a shaft between the threaded portion and the head, the head of the screw configured to be entirely disposed within the head hole of the epiphyseal head when the threaded portion of the screw cooperates with the internally threaded portion of the stem hole;
   wherein a proximal surface of the stem is planar about the internally threaded portion and a distal surface of the epiphyseal head is planar about the head hole;
   wherein at least portions of the proximal surface of the stem and the distal surface of the epiphyseal head are in contact when the epiphyseal head and the stem are assembled, and wherein the epiphyseal head comprises a lug that extends from the distal surface, the lug configured to be at least partially disposed within the stem hole when the epiphyseal head and the stem are assembled; and
   wherein the lug is cylindrical and the head hole extends through the lug.

2. The modular humeral prosthesis of claim 1, wherein one of the proximal surface of the stem and the distal surface of the epiphyseal head has a plurality of notches disposed according to a radial angular distribution about the longitudinal axis, and the other of the proximal surface of the stem and the distal surface of the epiphyseal head comprises a peg extending from said surface configured to cooperate with the plurality of notches.

3. The modular humeral prosthesis of claim 2, wherein, when implanted, the proximal surface of the stem and the distal surface of the epiphyseal head are located inside the humerus.

4. The modular humeral prosthesis of claim 2, wherein the distal surface of the epiphyseal head extends laterally beyond the stem at the plurality of angular positions.

5. The modular humeral prosthesis of claim 2, wherein each of the proximal surface of the stem and the distal surface of the epiphyseal head are substantially perpendicular to the longitudinal axis.

6. The modular humeral prosthesis of claim 1, wherein the stem comprises at least one longitudinal rib for rotational locking.

7. The modular humeral prosthesis of claim 1, wherein the stem hole is aligned with the longitudinal axis.

8. The modular humeral prosthesis of claim 7, wherein the stem hole has a first bore of a first diameter and a second bore that communicates with the first bore, the second bore having a second diameter that is smaller than the first diameter, and the lug is adapted to be at least partially disposed within the first bore of the stem.

9. The modular humeral prosthesis of claim 8, wherein second bore of the stem hole is threaded.

10. The modular humeral prosthesis of claim 1, wherein the head hole has a first bore of a first diameter and a second bore that communicates with the first bore, the second bore having a second diameter that is smaller than the first diameter.

11. The modular humeral prosthesis of claim 10, wherein at least a portion of the second bore of the head hole is threaded.

12. The modular humeral prosthesis of claim 11, wherein the stem hole has a first bore of a first diameter and a second bore that communicates with the first bore, the second bore having a second diameter that is smaller than the first diameter.

13. The modular humeral prosthesis of claim 12, wherein the at least a portion of the second bore of the stem hole is threaded.

* * * * *